United States Patent [19]

Kenny

[11] 4,456,004

[45] Jun. 26, 1984

[54] FRACTURE HOLDING

[76] Inventor: Charles H. Kenny, 276 South St., Pittsfield, Mass. 01201

[21] Appl. No.: 285,600

[22] Filed: Jul. 21, 1981

[51] Int. Cl.³ .............................................. A61F 5/04
[52] U.S. Cl. ................................................. 128/92 A
[58] Field of Search ................... 128/92 A, 84 R, 25; 403/141–146

[56] References Cited

U.S. PATENT DOCUMENTS

| | | | |
|---|---|---|---|
| 2,238,869 | 4/1941 | Haynes | 128/92 A |
| 2,238,870 | 4/1941 | Haynes | 128/92 A |
| 2,371,519 | 3/1945 | Haynes | 128/92 A |
| 2,391,537 | 12/1945 | Anderson | 128/92 A |
| 3,807,394 | 4/1974 | Atlenborough | 128/92 A |
| 3,961,854 | 6/1976 | Jaquet | 128/92 A |
| 3,977,397 | 8/1976 | Kalnberz et al. | 128/92 A |
| 4,360,012 | 11/1982 | McHarrie et al. | 128/92 A |

OTHER PUBLICATIONS

Howmedica Bulletin "The Original Hoffmann External Fixation System"; 1979.
Ace Orthopedic Advertisement "Ace Gives You A Choice", 1980–1981.
Ace Orthopedic Advertisement "The Ace-Fisher Fixator"; 1980–1981.
Edge et al., "External Fixation For Complicated Tibial Fractures", *The Journal of Bone and Joint Surgery*, Mar. 1981, pp. 92–97.

*Primary Examiner*—C. Fred Rosenbaum
*Assistant Examiner*—C. W. Shedd
*Attorney, Agent, or Firm*—Cushman, Darby & Cushman

[57] ABSTRACT

An external fixation assembly, and a method of treating fractures utilizing an external fixation assembly, are provided for facilitating the healing of fractured bones in a living body. Pins passing through bone portions are held stationary relative to each other by a frame which includes universal joints, articulation couplings, and adjustable length rods. Springs are provided in the assembly for applying compression to the universal joints allowing for the application of compression and the simultaneous application of axial loading to the bone portions. The universal joints and other components are arranged to provide free sliding of the components relative to each other upon loosening of the universal joints so that desired motion or force application at the fracture site may be provided.

21 Claims, 9 Drawing Figures

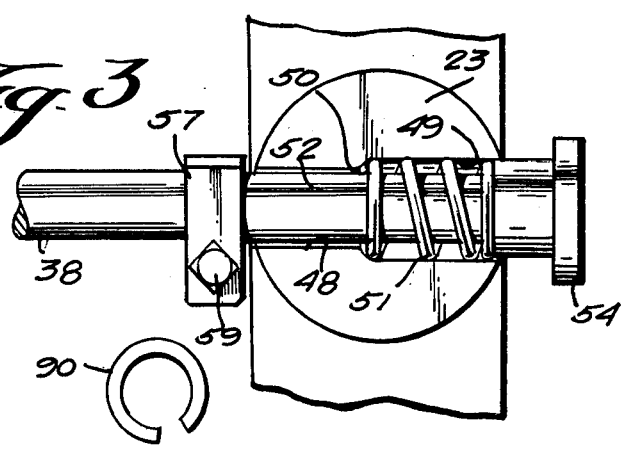
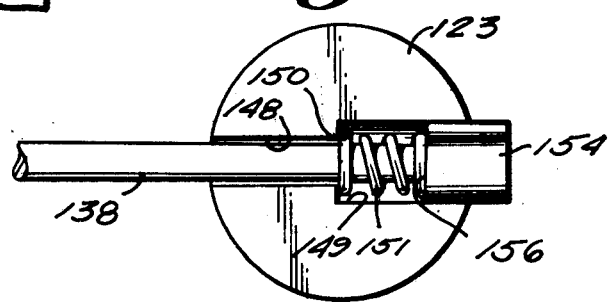
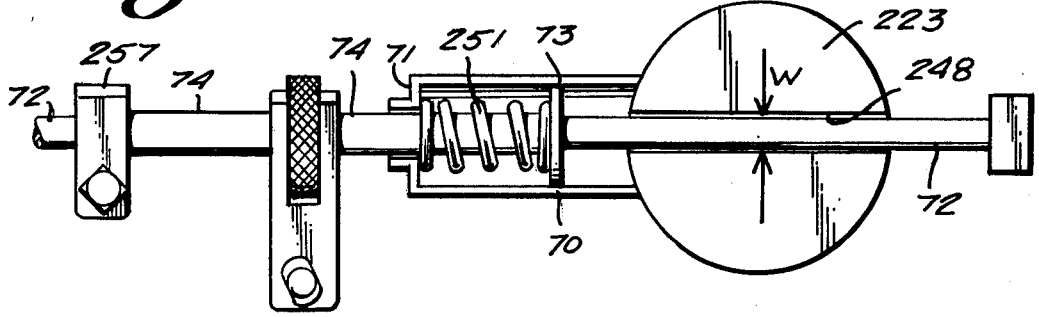
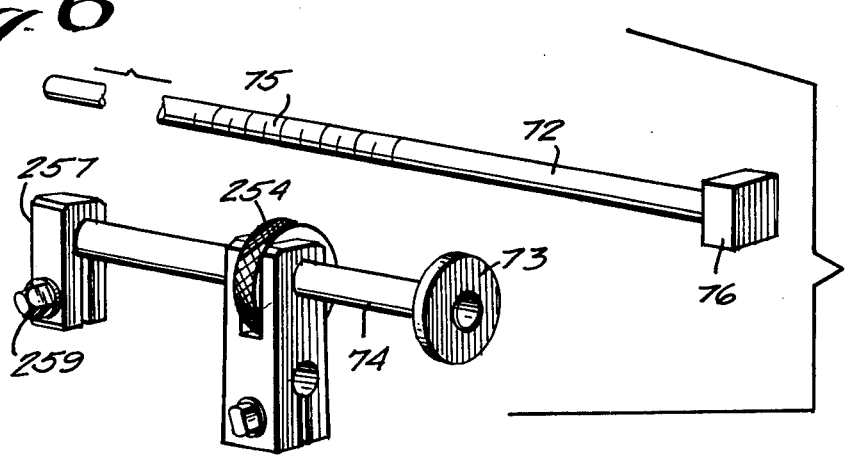

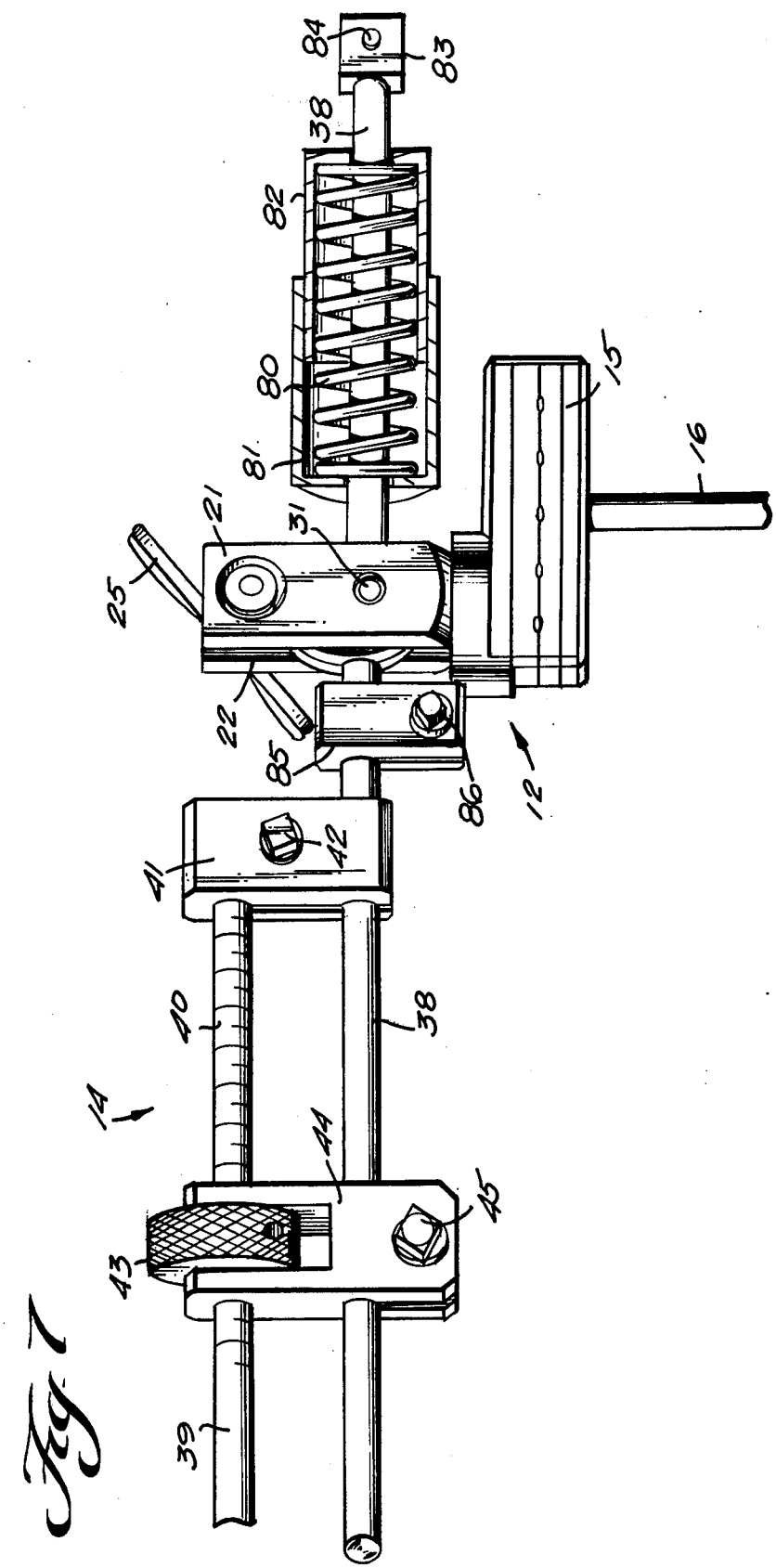

FRACTURE HOLDING

BACKGROUND AND SUMMARY OF THE INVENTION

The invention relates to improvements in an external fixation system for stabilizing fractured bones in a living body, component parts of such a system, and methods of facilitating bond healing utilizing such assemblies. There are a wide variety of external fixation systems on the market today, which systems are very useful in facilitating the healing of fractured bones. Such systems are most commonly employed where there is soft tissue loss in order to avoid infection, or where there is the necessity of repairing damaged blood vessels, or if it is necessary to retain joint mobility either above or below the fracture. Typical of successful prior art external fixation systems is one manufactured by ETS Jaquet Freres of Switzerland and distributed in the United States by Howmedica, Inc. of Rutherford, N.J.

While prior systems of external fixation are successful, under some circumstances there can be several drawbacks associated therewith. For instance under some circumstances the healing time for the fracture is unacceptably long, even to the extent that after initial stages of healing the external fixation system is removed and a cast is substituted. Such long healing times may result from inadequate compression applied to the fracture site. It is known that healing is facilitated when appropriate compression is applied to the fracture site, and when after initial healing intermittent axial loads are applied to the fracture site. Because prior external fixation systems perform their stabilizing functions so well, however, it has heretofore been difficult to develop a mechanism or method allowing compression and axial loading of the fracture site to facilitate healing.

According to the apparatus and method of the present invention, an external fixation assembly, and components parts therefor, are provided which provide the simultaneous application of axial loading and compression, facilitating healing so that long healing times associated with external fixation systems in some circumstances may be overcome. Also according to the present invention methods of facilitating fractured bone healing are provided which facilitate sliding of the external fixation frame components to allow, upon loosening of universal joint components of the frame, intermittent axial loads to be applied to the fracture site.

In its simplest terms, the apparatus according to the invention comprises the conventional frame components of universal joints, articulating couplings, and connecting rods with the addition of spring means for applying compressive forces directly to the universal joints. Adjustment of the compressive forces is easily effected utilizing knobs or the like readily accessible on the frame, and the amount of compression provided by the spring means may be positively controlled. Means may be provided for positively preventing distraction, if desired, or distraction can be opposed by the same spring compressive forces that provide the compression.

According to a basic method of the present invention, a fractured bone in a living body is stabilized by inserting pins into bone portions so that end portions of the pins extend externally of the body, and operatively attaching the universal joints, articulation couplings, and rods to the pins to provide the necessary frame for stabilizing the fracture. The method steps are practiced so that upon loosening of the universal joints coupled longitudinal, anterior-posterior, medial-lateral and torsional motion or force applications are provided, free sliding of the universal joints relative to each other also being provided so as to control static or dynamic loading of the fracture site and thereby minimize shear forces and maximize forces normal to the fracture plane.

According to another aspect of the method of the invention, a frame which extends externally of the body is operatively attached to bone portions of the fracture to stabilize the positions of the bone portions in a relative position where proper healing will take place. Predetermined, controlled compressive forces are applied with the frame to the fracture site to facilitate healing, and the frame—with internal compressive forces—is maintained in rigid position stabilizing the fracture and preventing substantially all relative movement between the bone portions until initial healing of the fracture takes place. The initial healing of the fracture must be sufficient to render the fracture capable of accepting intermittent axial loadings. Then the frame may be loosened sufficiently to allow intermittent axial loading of the fracture site while preventing destructive relative movements between the bone portions, and intermittent axial loads are applied to the fracture site to facilitate healing. When healing is substantially completed the frame is then removed. Displacement control of the frame is practiced to control the maximum amount of bone movement in response to intermittent axial loading.

It is the primary object of the present invention to provide improved apparatus and methods for facilitating healing of a fractured bone in a living body. This and other objects of the invention will become clear from an inspection of the detailed description of the invention and from the appended claims.

BRIEF DESCRIPTION OF THE DRAWINGS

FIG. 3 is a side schematic view, with one portion of the universal joint removed for clarity, of the structure of FIG. 2;

FIG. 4 is a side view like that of FIG. 3 illustrating another exemplary embodiment of compressive force applying means according to the invention;

FIG. 5 is a side schematic view like that of FIG. 3 illustrating another exemplary embodiment of compressive force application means according to the invention;

FIG. 6 is an exploded view of some key components of the FIG. 5 embodiment;

FIG. 7 is a side perspective view illustrating an assembly according to the present invention having another exemplary compressive force application means associated therewith;

DETAILED DESCRIPTION OF THE DRAWINGS

Figure 1:
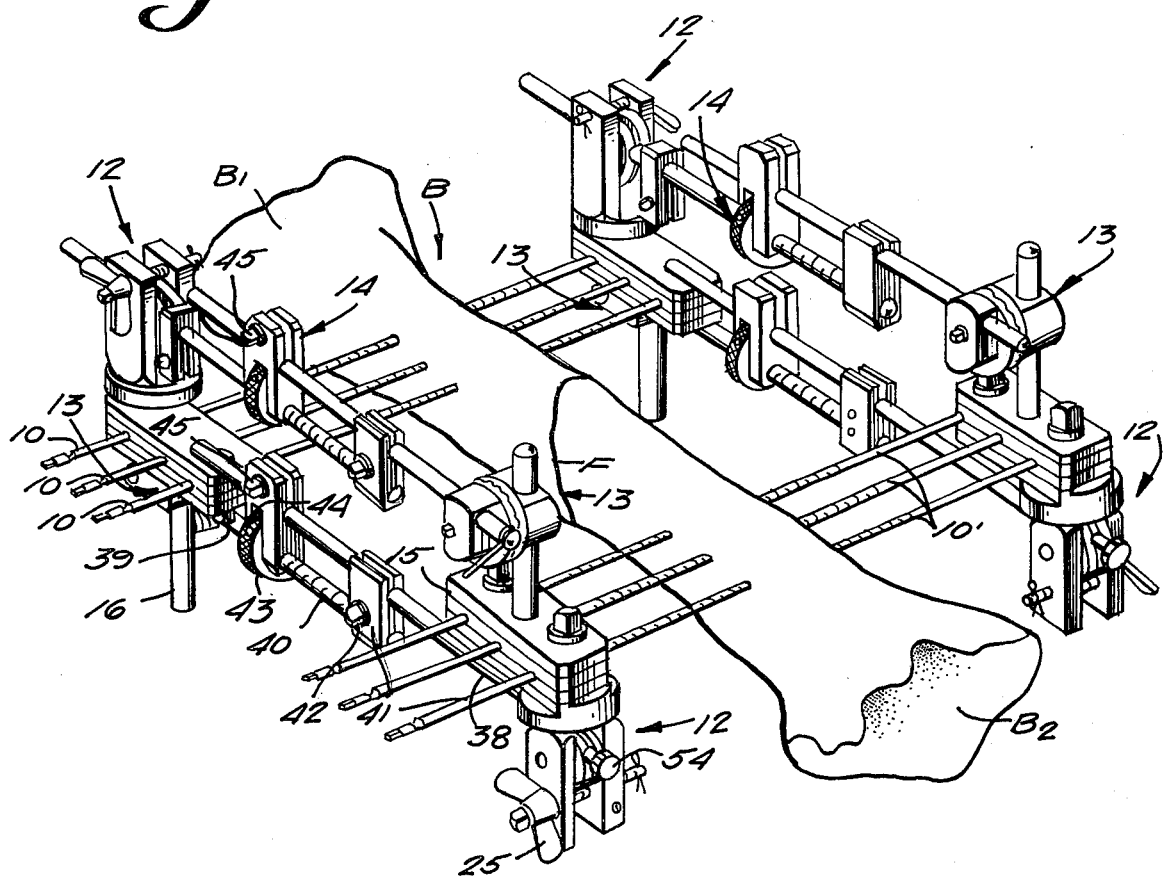
FIG. 1 is a perspective schematic view illustrating an exemplary external fixation assembly according to the present invention in use for stabilizing a fractured bone.

Conventional external fixation system, such as one manufactured by ETS Jaquet Freres of Geneva, Switzerland and distributed by Howmedica, Inc. of Rutherford, N.J., include a number of conventional components. Among these components are: Transfixing pins, a plurality of which pins 10 are caused to penetrate (in conventional fashion) a first portion B1 of a bone B having a fracture site F, and a second plurality of such pins 10' which are utilized to penetrate a second portion B2 of the bone B. A plurality of universal joint means 12. A plurality of articulation couplings 13. And, a plurality of adjustable-length connecting rods 14. These basic components, as well as variations thereof, are provided for stabilizing the positions of the pins 10, 10' to prevent any substantial movement of the bone B. Each universal joint 12 conventionally includes clamping plates 15 for receiving and clamping the pins 10, 10' therein and an integral oppositely-extending rod 16.

The universal joint means 12 provide the primary attachment between the pins and the frame, and provide for relative rotational movement of the connecting-rod receiving portion thereof relative to the integral pin-receiving portion 15 thereof about two different axes. Components of a conventional universal joint include the base 20 (see FIG. 2), a pair of half-clamp members 21, 22, a pair of rod-receiving discs 23, 24, and a wing screw 25 for releasably clamping the components together. The base member 20 includes a ridge portion 26 adapted to receiving tapered flange portions 27, 28 formed on the half-clamp members 21, 22, respectively. Each half-clamp member also has an opening formed therein for receipt of a shaft from its respective disc 23, 24 which mounts the respective disc for relative rotation with respect to the half-clamp member. Only the opening 29 associated with half-clamp member 22 and the shaft 30 associated with disc 24 can be seen in FIG. 2. Shaft 31 associated with disc 23 can be seen in FIG. 7. Further, a smooth bore opening 32 is provided in the half-clamp member 22, while an opening 33 containing a pivotally mounted screw-threaded nut 34 is provided in the half-clamp member 21. The threaded portion of the wing screw 25 passes through the opening 32 into engagement with the nut 34 and when tightened into engagement therewith clamps the component 20 through 24 together. When loosened, the components 21, 22 can rotate about a central axis A—A extending through the base 20, while the discs 23, 24 can rotate about the common axis B—B defined by their shafts 30, 31. Only conventional components of the universal joint 12 illustrated in FIG. 2 have been described so far, features according to the present invention to be described later.

The articulation couplings 13 provide for reinforcement of the frame by providing a coupling between the rod portion 16 of a universal joint means 12 and a connecting rod 14. An articulation coupling when loosened allows insertion of the rod portion 16 and a portion of rod means 14 through the openings therein, and provides for relative rotational movement therebetween about an axis extending perpendicular to a plane substantially containing the rods when received by the openings.

The adjustable connecting rods 14 illustrated in FIG. 1 are the most useful, although under some circumstances for some enivonments rods having no length adjustment capability may be utilized. The rods 14 comprise as their basic parts (see FIG. 1 in particular) a first portion 38; a second portion 39 having screw threads 40 formed thereon; a clamp 41 affixed to the end of the screw threaded portion 40 and receiving the rod portion 38 at the other end thereof, and having a bolt 42 that may be loosened or tightened to alternately allow sliding or no sliding of the clamp 41 with respect to the rod portion 38; an internally threaded wheel 43 receiving the thread portion 40; and a clamp 44 receiving the wheel 43 at one end thereof and the rod portion 38 at the other end thereof and having a bolt 45 that may be loosened or tightened to provide sliding or no sliding of the clamp 44 with respect to the rod 38, respectively.

Conventional components and their external fixation system having been described, exemplary components parts and assemblies according to the present invention will now be set forth:

It is desirable to facilitate healing at the fracture site F to be able to apply compression to the site F. It is also desirable to be able to provide the simultaneous application of axial loading to the site F. According to the present invention, mechanical means are provided for applying the appropriate compression. In the first embodiment of such means illustrated in FIGS. 1 through 3, spring means are provided for applying a predetermined, defined compressive force to at least one universal joint means 12 of a stabilizing frame to hold the bone portions B1, B2 together under force. The discs 23, 24 of the universal joint means 12 are especially formed for this application, and additional components are provided.

Figure 2:
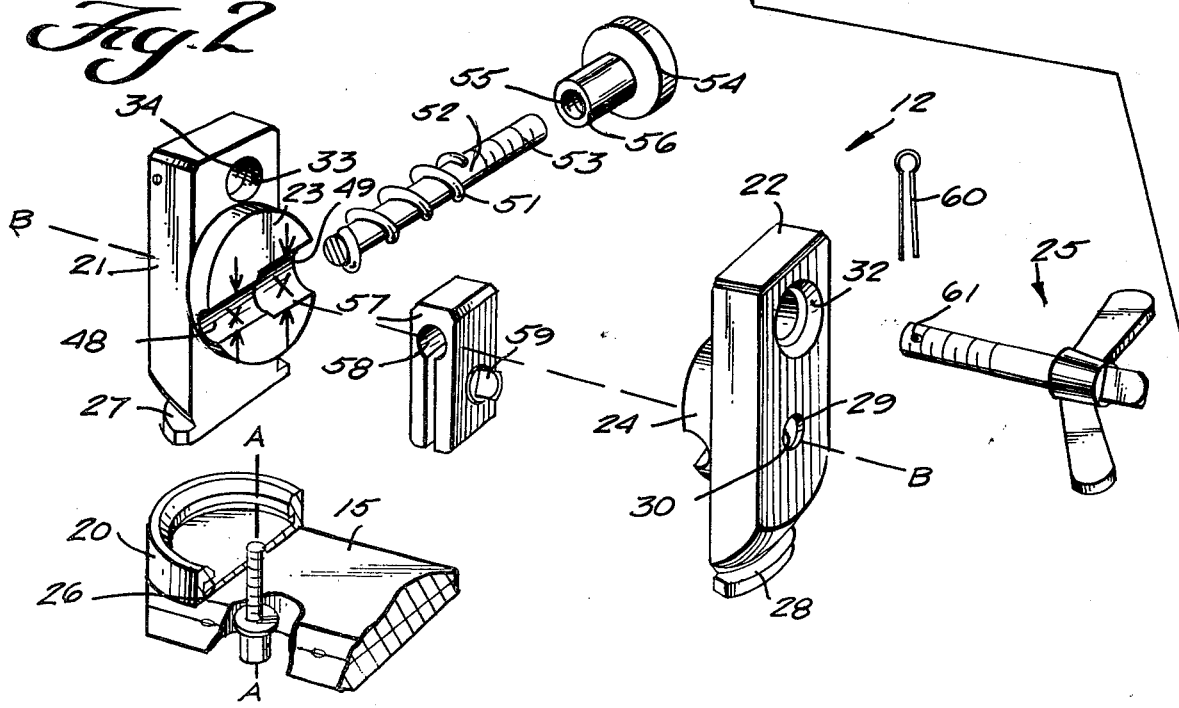
FIG. 2 is an exploded perspective detail view of an exemplary universal joint and compressive force application means of the assembly of FIG. 1.

As seen most clearly in FIGS. 2 and 3, each of the discs 23, 24 is formed so that an arcuate cutout, or substantially semi-circular slot having a first portion 48 of width or diameter x, and having a second portion 49 of width or diameter X, wherein X is greater than x. The interface 50 between the portions 48, 49 provides an abutment for a first end of a coil spring 51 having an outside diameter about the same as, or slightly less than, the dimension X. The spring 51 applies a spring force to the universal joint 12 at the interface 50.

The spring means further comprise means accessible from the exterior of the universal joints adjacent the disc cutouts 49 for adjusting the compression of the spring 51. In the embodiment illustrated in FIGS. 1 through 3, this is provided by a short rod 52 which is received by the first cutout portions 48 and has an external thread 53 formed in one end thereof. A knob 54 having internal threading 55 is in operative engagement with the rod 52, and has a shoulder portion 56 which comprises an abutment which engages a second end of the spring 51 and effects compression, or allows elongation, thereof depending upon the relative position of the knob 54 with respect to the rod 52. As can be seen, the knob 54 may be maintained entirely exterior of the universal joint means 12 and readily accessible therefrom.

At the opposite end of the short rod 52 a clamp 57 is provided. The clamp 57 has an internal opening 58 large enough to receive the rod portion 52, and also to receive the rod portion 38 of the adjustable length rod means 14. By loosening bolt 59 the clamp can be loosened or tightened to either positively be clamped at a relative position along the rod 52, holding the rod 38, or to allow detachment of the rod portions 38, 52 and relative movement along one or both. By forming the compression means in such a way, as illustrated in FIG.

2, an integral unit is provided which is readily connectable up to conventional adjustable length rod means 14.

With respect to FIG. 2, one further difference of the universal joint means 12 from the prior art is illustrated. In order to prevent the screw nut 25 from being completely detached from the half-clamp members 21, 22, a cotter pin 60 can be passed through an end opening 61 thereof.

The embodiment illustrated in FIG. 4 is similar to that illustrated in FIG. 3 with like structures being indicated by like reference numerals except that they are preceded by the number "1". In this embodiment, however the shoulder (abutment) element 156 is a piston formed at the end of a rod portion 138 of an otherwise conventional adjustable-length rod means 114. In this embodiment adjustment of spring 151 tension is provided by the adjustment of rod 138 by rod means 114.

In FIGS. 5 and 6 another embodiment of component parts according to the invention for providing a predetermined, defined compressive spring force is illustrated. In this embodiment components functionally similar to those in the FIGS. 2 and 3 embodiment are identified by like numerals only with the preceding numeral "2".

In this embodiment a half cylinder 70 is rigidly connected to disc 223 and its corresponding disc (not shown). One end of the spring 251 abuts against an interior end wall 71 of the two parts 70 (which end wall 71 is slidable over rod portion 72), while the other end of the spring 251 abuts against enlarged end 73 of a rod portion 72. The tubular portion 74 receives the rod portion 72 therein, the rod portion 72 having a screw threaded end 75 received by internal threads of wheel 274. The end of rod portions 72 opposite screw threaded portions 75 includes an enlarged head 76 which is larger than the width W of the arcuate cutout or substantially semi-circular slot 248 in disc 223. Clamp 257 with bolt 259 corresponds in function to clamp 57 with bolt 59 of the FIGS. 2 and 3 embodiment.

FIG. 7 illustrates another exemplary embodiment of a compression force applying means according to the present invention illustrated in conjunction with a conventional universal joint means 12 and adjustable length rod means 14. In this embodiment the compressive force is provided by a coil spring 80 which encircles rod portion 38 and is received by a pair of telescopic housing portions 81, 82 which slide relative to each other and relative to the rod portion 38. The exterior of telescopic housing portion 82 may have indicia formed thereon to indicate the degree of compression of spring 80. An end stop 83 is preferably releasably attached by holding screw 84 to the end of rod portion 38 distal from the rod portion 39, and preferably an adjustable clamp 85 is provided on the side of universal joint means 12 opposite the spring 80, and between the universal joint means 12 and the slide 41. By loosening or tightening the bolt 86 associated with stop 85 its position along the rod 38 may be adjusted or fixed, respectively.

Figure 8:
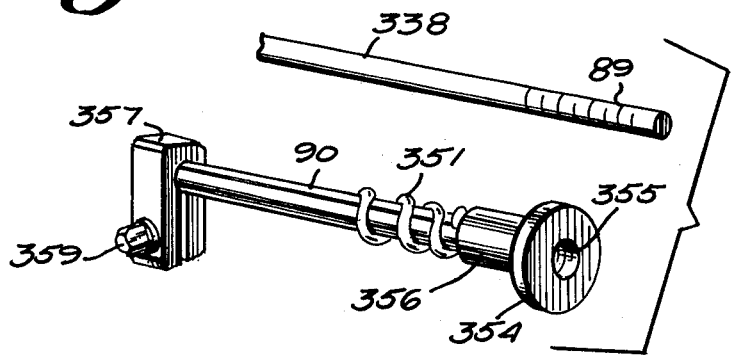
FIG. 8 is a perspective expoded view illustrating a further exemplary embodiment of compressive force application means according to the invention.
Figure 9:
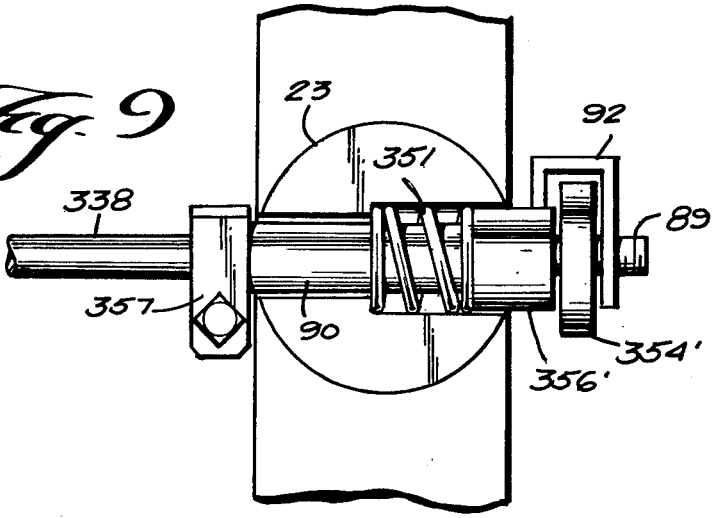
FIG. 9 is a view like FIG. 3 only showing a modified form of the compressive force application means of FIG. 8.

In the FIG. 8 embodiment, components generally functionally similar to those in the FIGS. 2 and 3 embodiments are identified by like numerals only with the preceding numeral "3". In this embodiment, the knob 354 and shoulder 356 are integral with a tube 90, which is also integral with clamp 357. A rod 338, with threaded end 89, passes through tube 90 and is engaged by internal screw-threading 355 of knob 354, threads 355 and 89 engaging. FIG. 9 shows this general structure in association with a universal joint; the structure in FIG. 9 differs from that in FIG. 8 only in that the knob 354' is not integral with the shoulder portion 356' but freely engages the threaded portion 89 of rod 338. A bracket 92 extending from should portion 356' (straddling knob 354') and receiving rod 338 (rod 338 passes through bracket 92, not being in screw-threaded engagement therewith) prevents movement of knob 354' along rod 338. The modification in FIG. 9 has the advantage—compared to the FIG. 8 structure—that rotation of knob 354' to adjust the spring 351 compression does not effect rotation of the entire structure (i.e. shoulder 356, tube 90, and clamp 357).

The compressive force applying means described above with respect to FIGS. 2 through 9 may be utilized essentially wherever conventional universal joint means and/or connection rod means are utilized in conventional external fixation systems. While the invention has been described with respect to particular universal joint means, articulation couplings, and adjustable-length rod means, it is to be understood that the invention is equally practicable with other types of frame components for an external fixation system, and the invention is not limited to the specific components illustrated.

An exemplary manner in which the mechanical means for applying compression to the fracture site according to the present invention are utilizable in an external fixation system will now be described with particular reference to FIG. 7, it being understood that the other embodiments function similarly.

With the pin-receiving portion 15 of the universal joint means 12 of FIG. 7 receiving pins 10 (or 10'), and the rod 16 in rod portion 39 otherwise appropriately connected up to frame components, a compressive force is applied to the fracture site F by turning wheel 43 to effectively bring end stop 83 into engagement with housing portion 82, and housing portion 81 into engagement with universal joint means 12. Wheel 43 is turned until the desired degree of compression of spring 80 is obtained, as by reading inidica on the exterior of the housing portion 82, and then the bolt 42 is tightened. The universal joint 12 may then also be tightened down, utilizing wing screw 25. However if axial intermittent loading of the fracture site F is also desirable, the universal joint 12 is not tightened completely, but is left loose. If maximum displacement of the bone portions B1, B2 under intermittent axial loading is to be provided, the stop 85 bolt 86 is loosened, the stop 85 is slid to the position with respect to the universal joint means 12 defining the maximum displacement, and then the bolt 86 is tightened down.

For each of the embodiments described above with respect to FIGS. 2 through 9 further means for displacement control and/or distraction-prevention may be provided. Such means may take the form of polyethylene snap-washers of different thickness, such as the snap-washer 90 illustrated in FIG. 3 which would be insertable between discs 23, 24 and the clamp 57.

The arrangement of the component parts of the frame illustrated in FIG. 1 of the drawings is novel. The relative positioning between component parts allows, upon loosening of the universal joints 12, free sliding of the universal joints relative to each other. In prior constructions such free sliding was not possible since there would be binding of various component parts which prevented it. Such free sliding is desirable since it allows the application of intermittent axial loads to the fracture site F, facilitating healing. Upon loosening of the universal joints, coupled longitudinal, anterior-posterior, medial-lateral and torsional motion or force application at the fracture site are provided, so that static or dynamic loading of the fracture site with resulting minimization of shear forces and maximization of forces normal to the fracture plane are provided thus increasing stability under loading.

The relative position of the articulating couplings 13 along the rod 16 changes the angular relationship of the components, and that can be taken advantage of to impart forces normal to the plane of fracture.

Such advantageous procedures are provided by the frame illustrated in FIG. 1 by providing direct connection utilizing a rod means 14 between a universal joint means 12 and an articulating coupling 13, rather than connecting two articulation couplings and two universal joint means together as is common in the prior art. Such connections are preferably provided on both sides of a bone B where a dual type frame structure is desirable, as is common in the fixation of a fractured tibia. The technique according to the invention is practicable in other type of frame mountings aside from that illustrated in FIG. 1, however, such as in mountings where some pins do not extend completely through bone portions, but rather transversely extending half-pins are provided. Further, this aspect of the invention may be practiced utilizing conventional universal joints and like components, although it is preferred that the compressive force application means according to the invention (as described with respect to FIGS. 2 through 9) be utilized.

In practicing a typical method of facilitating proper healing of a fracture of a bone B in a living body, a method according to the present invention comprises the steps of substantially sequentially: Operatively attaching a frame (e.g. pins 10, 10'; universal joint means 12; couplings 13; rods 14), which extends externally of the body, to the bone portions B1 and B2 of the fracture to stabilize the positions of the bone portions B1, B2 in a relative position wherein proper healing at the fracture site F will take place. Applying predetermined, controlled compressive forces with the frame to the fracture site to facilitate healing, as by adjusting knob 54 to provide the appropriate compression of spring 51 at each universal joint means 12, and then; maintaining the frame, with internal compressive forces, in rigid position stabilizing the fracture by tightening down the wing screws 25 of each of the universal joints 12. This prevents substantially all relative movement between the bone portions B1, B2 until initial healing of the fracture takes place—i.e. sufficient healing to render the fracture capable of accepting intermittent axial loads. This normally takes about 2 to 4 weeks. Then the frame is loosened, by loosening the wing screws 25 of all the universal joint means 12, sufficiently to allow intermittent axial loading of the fracture site F while preventing destructive relative movements between the bone portions. Preferably the maximum amount of bone movement as a result of intermittent axial loading is controlled by utilizing polyethylene snap-washers 90 or the like to limit the movement of the universal joint means 12. [In the FIG. 7 embodiment this would be accomplished by moving the stop 85]. Intermittent axial loads are then applied to the fracture site F to facilitate healing. For instance where the bone B is a tibia, the intermittent axial loads are applied by allowing the patient to stand up and apply some weight to his/her leg for brief, intermittent periods (as by walking). In this way proper healing of the bone B can take place relatively quickly, and the frame need not be removed until substantially complete healing at the fracture site F has taken place.

It will thus be seen that according to the present invention an assembly, assembly components, and methods have been provided which facilitate the proper healing of a fractured bone in a living body. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. An external fixation assembly for stabilizing a fractured bone in a living body to facilitate proper healing at the fracture site, comprising:

a plurality of pins for penetrating each portion of a fractured bone; and means for stabilizing the position of said pins externally of the body so that the bone portions are maintained in proper healing position, said means comprising mechanical means for applying compression and for providing for the simultaneous application of axial loading to the fracture site, said stabilizing means comprising a plurality of universal joint means; a plurality of articulation coupling means; a plurality of rod means for operatively interconnecting said pins, universal joint means, and articulation coupling means, including a rod received by each universal joint means and interconnecting said universal joint means to an articulation coupling means; and spring means for applying a predetermined defined compressive force directly to at least one of said plurality of universal joint means, acting between said universal joint means and said rod received thereby, so that the bone portions are held together by the compressive force of said spring means.

2. An assembly as recited in claim 1 wherein each of said universal joint means comprises a pair of rod-receiving pivotal discs each mounted in a rotatable half-clamp member; each of said discs having a rod-receiving substantially semi-circular slot formed therein, each slot having a first portion of a diameter x, and a second portion of a diameter X, wherein X is greater than x; said spring means comprising a coil spring received by said disc slots second portions and abutting an interface between said disc slot first and second portions at a first end thereof and an abutment at a second end thereof, applying a spring force to said universal joint at said interface.

3. An assembly as recited in claim 2 wherein said spring means further comprises means accessible from the exterior of each said universal joint adjacent said disc cutouts second portions for adjusting the compression of said spring means and thereby the force said spring means apply to each said universal joint, said means including said abutment at said second end of said spring.

4. An assembly as recited in claim 3 wherein said spring compression adjusting means comprises said rod, a portion of said rod being received by said disc slot first portions and passing through the interior of said coil spring, and having an externally threaded end extending outwardly from said coil spring adjacent thereto; and an internally threaded knob received by said rod portion threaded end, said knob having a shoulder portion comprising said abutment abutting said second end of said coil spring.

5. An assembly as recited in claims 3 or 4 further comprising a clamp means for limiting the movement of each said universal joints, said clamp means disposed on the opposite side of a said universal joint as said spring compression adjusting means.

6. An assembly as recited in claim 3 wherein said spring compression adjusting means comprises a tube received by said disc slot first portions and passing through the interior of said coil spring; said rod having an externally threaded end passing through said tube and extending outwardly from said tube; an internally threaded knob received by said rod threaded end; and a shoulder portion integral with said tube comprising said abutment and abutting said second end of said coil spring.

7. An assembly as recited in claim 1 wherein each said rod includes a first rod portion extending through a said universal joint means and received thereby, a second rod portion, and means for adjusting the relative positions of said first and second portions with respect to each other, and thus the effective length of said rod, interconnecting said first and second rod portions; and wherein said spring means includes a coil spring surrounding each said first rod portion and disposed on the opposite side of a said universal joint as said rod portions position-adjusting means.

8. An assembly as recited in claim 7 wherein each said spring means further comprise a spring stop formed on the end of said first rod portion opposite said rod portions relative position-adjusting means; and wherein said coil spring is disposed within a pair of telescopically engaging housing portions slidable on said first rod portion.

9. An assembly as recited in claims 7 or 8 further comprising means for limiting the movement of each said universal joint means, said limiting means comprising an adjustable-position clamp disposed on said first rod portion on the opposite side of said universal joint means as said coil spring, between said universal joint and said relative rod portions position-adjusting means.

10. An assembly as recited in claim 1 further comprising displacement controlling means associated with said mechanical means.

11. An assembly as recited in claim 1 wherein each of said universal joint means comprises a pair of rod-receiving pivotal discs each mounted in a rotatable half-clamp member, each of said discs having a half-tubular housing portion integral therewith and extending outwardly therefrom; said spring means comprising a coil spring received by said integral tubular housing portions, and said rod disposed concentrically of said coil spring, said rod passing through said tubular housing portion and having an abutment means formed thereon, said coil spring being retained between said abutment means and between an end face of said tubular housing portions.

12. An external fixation assembly for stabilizing a fractured bone in a living body to facilitate proper healing at the fracture site, comprising:
  a plurality of pins for penetrating each portion of a fractured bone; and
  means for stabilizing the position of said pins externally of the body so that the bone portions are maintained in proper healing position, said means comprising: a plurality of universal joint means; a plurality of articulation coupling means; a plurality of rod means for operatively interconnecting said pins, universal joint means, and articulation coupling means, including a rod received by each universal joint means and interconnecting said universal joint means to an articulation coupling means; and spring means for applying a predetermined defined compressive force directly to at least one of said plurality of universal joint means, acting between said universal joint means and said rod received thereby, so that the bone portions are held together by the compressive force of said spring means.

13. An assembly as recited in claim 12 wherein each of said universal joint means comprises a pair of rod-receiving pivotal discs each mounted in a rotatable half-clamp member; each of said discs having a rod-receiving substantially semi-circular slot formed therein, each slot having a first portion of a diameter x, and a second portion of a diameter X, wherein X is greater than x; and said springs means comprising a coil spring received by said disc slots second portions and abutting an interface between said disc slot first and second portions at a first end thereof and an abutment at a second end thereof, applying a spring force to said universal joint at said interface.

14. An assembly as recited in claim 13 wherein said spring means further comprises means accessible from the exterior of each said universal joint adjacent said disc cutouts second portions for adjusting the compression of said spring means and thereby the force said spring means apply to each said universal joint, said means including said abutment at said second end of said spring.

15. An assembly as recited in claim 14 wherein said spring compression adjusting means comprises a tube received by said disc slot first portions and passing through the interior of said coil spring; said rod having an externally threaded end passing through said tube and extending outwardly from said tube; an internally threaded knob received by said rod threaded end; and a shoulder portion integral with said tube comprising said abutment and abutting said second end of said coil spring.

16. An assembly as recited in claim 12 wherein each said rod includes a first rod portion extending through a said universal joint means and received thereby, a second rod portion, and means for adjusting the relative positions of said first and second portions with respect to each other, and thus the effective length of said rod, interconnecting said first and second rod portions; and wherein said spring means includes a coil spring surrounding each said first rod portion and disposed on the opposite side of a said universal joint as said rod portions position-adjusting means.

17. An assembly as recited in claim 16 wherein each said spring means further comprise a spring stop formed on the end of said first rod portion opposite said rod portions relative position-adjusting means; and wherein said coil spring is disposed within a pair of telescopically engaging housing portions slidable on said first rod portion.

18. An assembly as recited in claim 12 wherein each of said universal joint means comprises a pair of rod-receiving pivotal discs each mounted in a rotatable half-clamp member, each of said discs having a half-tubular housing portion integral therewith and extending outwardly therefrom; said spring means comprising a coil spring received by said integral tubular housing portions, of said rod and a rod portion disposed concentrically of said coil spring, said rod portion passing through said tubular housing portion.

19. An assembly as recited in claim 18 wherein said rod portion comprises a tube, and further comprising a rod having an externally threaded end passing through said tube and extending outwardly therefrom; an internally threaded knob received by said rod threaded end; and a shoulder portion integral with said tube and abutting an end of said coil spring, said spring being held between said shoulder and an end face of said tubular housing portions.

20. An assembly as recited in claim 19 further comprising a clamp integral with said tube on the opposite side thereof as said knob, and a bracket extending from said shoulder portion straddling said knob to receive said rod, said knob being distinct from said tube and bracket.

21. An external fixation assembly for stabilizing a fractured bone in a living body to facilitate proper healing at the fracture site, comprising:
   a plurality of pins for penetrating each portion of a fractured bone; and
   means for stabilizing the position of said pins externally of the body so that the bone portions are maintained in proper healing position, said means comprising mechanical means for applying compression and for providing for the simultaneous application of axial loading to the fracture site, said stabilizing means comprising a plurality of universal joint means; a plurality of articulation coupling means; a plurality of rod means for operatively interconnecting said pins, universal joint means, and articulation coupling means; and spring means for applying a predetermined defined compressive force directly to at least one of said plurality of universal joint means so that the bone portions are held together under force; the improvement comprising a said universal joint means which comprises: a pair of rod-receiving discs each mounted between two rotatable half-clamp members; each of said discs having a rod-receiving substantially semicircular slot formed therein; said discs being pivotally positionable so that said slots are generally alignable in opposition so as to form a substantially cylindrical opening between said clamp members; said opening having a first portion of a diameter x, and a second portion of a diameter X, wherein X, is greater than x; said spring means comprising a coil spring received in said opening second portion and abutting an interface between said opening first and second portions at a first end thereof and an abutment carried on said rod at a second end thereof, thereby applying a spring force to said universal joint at said interface.

* * * * *